(12) United States Patent
Caldarelli et al.

(10) Patent No.: US 6,906,199 B2
(45) Date of Patent: Jun. 14, 2005

(54) PROCESS FOR PREPARING DISTAMYCIN DERIVATIVES

(75) Inventors: Francensco Caldarelli, Milan (IT); Lucio Ceriani, Parariago (IT); Ilaria Candiani, Busto Arsizio (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 10/415,091

(22) PCT Filed: Nov. 7, 2001

(86) PCT No.: PCT/EP01/13050

§ 371 (c)(1),
(2), (4) Date: Sep. 3, 2003

(87) PCT Pub. No.: WO02/44147

PCT Pub. Date: Jun. 6, 2002

(65) Prior Publication Data

US 2004/0077550 A1 Apr. 22, 2004

(30) Foreign Application Priority Data

Nov. 28, 2000  (GB) .............................................. 0029004

(51) Int. Cl.$^7$ ............................................. A61K 31/415
(52) U.S. Cl. ....................... 548/537; 530/332; 530/300; 530/333; 514/18; 514/19; 514/20; 548/312.4; 548/312.7; 548/313.1; 548/314.7; 548/364.1; 548/365.1; 548/518
(58) Field of Search ................................. 530/333, 300; 514/18, 19, 20; 548/537, 312.4, 312.7, 313.1, 314.7, 364.1, 365.1, 518

(56) References Cited

U.S. PATENT DOCUMENTS

| 5,646,177 A | 7/1997 | Koch et al. |
| 5,880,097 A | 3/1999 | Lyttle et al. |

FOREIGN PATENT DOCUMENTS

| EP | 0 246 868 A1 | 11/1987 |
| EP | 0 265 719 A1 | 5/1988 |
| EP | 0 388 948 A1 | 9/1990 |
| EP | 0 420 121 A1 | 4/1991 |
| WO | 90/11277 | 10/1990 |
| WO | 96/05196 | 2/1996 |
| WO | 97/43258 | 11/1997 |
| WO | 98/04524 A1 | 2/1998 |
| WO | 98/21202 A1 | 5/1998 |
| WO | 99/34796 A1 | 7/1999 |
| WO | 99/50265 A1 | 10/1999 |
| WO | 99/50266 A1 | 10/1999 |
| WO | 00/06541 A1 | 2/2000 |
| WO | 00/06542 | 2/2000 |

OTHER PUBLICATIONS

Cozzi P et al.: "Cytotoxic alpha–bromoacrylic derivatives of distamycin analogues modified at the amidino moiety," Bioorganic & Medicinal Chemistry Letters, Oxford, GB, vol. 10, No. 11, Jun. 2000.

XP–001039783: "Elevation of Placental Glutathione S–Tranferase Form (GST–π) in Tumor Tissues and the Levels in Sera of Patients with Cancer," Tsuchida et al., Cancer Research 49, pp. 5225–5229, Sep. 15, 1989.

XP–001039581: "Synthesis and Antitumor Activity of New Benzoheterocyclic Derivatives of Distamycin A," Baraldi et al., J. Med. Chem. 2000, 43, pp. 2675–2684, Jun. 27, 2000.

XP–001039865: #5240 In Vivo Induction of Apotosis with PNU–166196 In Human Ovarian Carcinoma Xenografts, Giusti et al., Pharmacia & Upjohn, Nerviano (Mi), Italy, p. 825, Mar. 2000.

XP–001039805: "A new class of cytotoxic DNA minor groove binders: α–halogenoacrylic derivatives of pyrrole-carbamoyl oligomers," Paolo Cozzi, II Farmaco 56 (2001) 57–65.

XP–001039737: "Non–chemotherapeutic agents that potentiate chemotherapy efficacy," David J. Stewart and William K. Evans, Cancer Treatment Reviews (1989) 16: 1–40.

XP–002104215: "The antitumor efficacy of cytotoxic drugs is potentiated by treatment with PNU 145156E, a growth-factor–complexing molecule," Sola et al., Cancer Chemother Pharmacol (1999) 43: 241–246.

XP–002110339: "Gemcitabine: Future Prospects of Single-Agent and Combination Studies," Van Moorsel et al., Department of Medical Oncology, University Hospital Vrije Universiteit, Amsterdam, The Netherlands, pp. 127–134, 1997.

"Cytotoxic Halogenoacrylic Derivatives of Distamycin A," P Cozzi et al., Bioorganic & Medicinal Chemistry Letters 10(2000) 1269–1272.

(Continued)

Primary Examiner—Bruce R. Campell
Assistant Examiner—Andrew D. Kosar
(74) Attorney, Agent, or Firm—Scully, Scott, Murphy & Presser

(57) ABSTRACT

It is described a process for preparing, in high yields and purity and without the need of carrying out several steps and/or isolating many intermediates which could lead to undesired by-products, a distamycin derivative of formula (I)

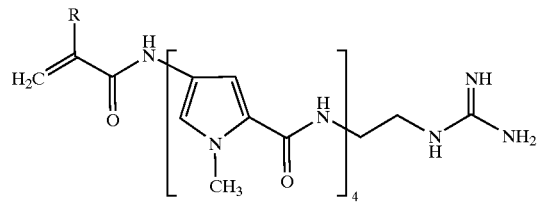

wherein R is a bromine or chlorine atom; or a pharmaceutically acceptable salt thereof. The compounds of formula (I) are useful in therapy as antitumor agents.

15 Claims, No Drawings

OTHER PUBLICATIONS

XP-002104217: "Distamycin-A Derivatives Potentiate Tumor-Necrosis-Factor Activity Via the Modulation of Tyrosine Prosphorylation," Int. J. Cancer: 72, 810–814 (1997).

XP-000671766: "Structure–Activity Relationship of Novel Distamycin A Derivatives: Synthesis and Antitumor Activity," D'Alessio et al., Bioorganic & Medical Chemistry Letters, vol. 4, No. 12, pp. 1467–1472, 1994.

XP-002191966: "Fluorosulfonic Acid," p. 740, Paragraph 4206 (2001).

XP-001039733: "Mismatch repair deficiency is associated with resistance to DNA minor groove alkylating agents," British Journal of Cancer (1999) 80 (3/4), 338–343.

XP-001039861: #2708 "Antitumor Activity of PNU–166196, A Novel DNA Minor Groove Binder Selected for Clinical Development," Geroni et al., pp. 425–426, Mar. 2000.

Original Paper, "Combination of the New Minor Groove Alkylator Tallimustine and Melphalan," Tagliabue et al., European Journal of Cancer, vol. 33, No. 2, pp. 284–287, 1997.

XP-002181404: "Total Synthesis of Distamycin A and 2640 Analogues: A Solution–Phase Combinatorial Approach to the Discovery of New, Bioactive DNA Binding Agents and Development of a Rapid, High–Throughput Screen for Determining Relative DNA Binding Affinity or DNA Binding Sequence Selectivity," Boger et al., J. Am. Chem. Soc. 2000, 122, 6382–6394.

"Synthesis and Antitumor Activity of Novel Distamycin Derivatives," Bioorganic & Medicinal Chemistry Letters, vol. 6, No. 11, pp. 1241–1246, 1996.

"Combination Therapy with Gemcitabine in Non–small Cell Lung Cancer," Mosconi et al., European Journal of Cancer, vol. 33, Suppl. 1, pp. 514–517, 1997.

XP-001039871: "PNU–166196: A Novel Antitumor Agent Whose Cytotoxicity is Enhanced in Tumor Cells with High Levels of Glutathione," Geroni et al., pp. 41–42, Jul. 2000.

PROCESS FOR PREPARING DISTAMYCIN DERIVATIVES

BACKGROUND OF THE INVENTION

1. Field of the Invention

The present invention relates to a process for preparing distamycin derivatives and, more in particular, it relates to a process for preparing acryloyl-distamycin-guanidino derivatives, known to possess a remarkable antitumor activity.

2. Description of the Related Art

Distamycin A, whose formula is reported below

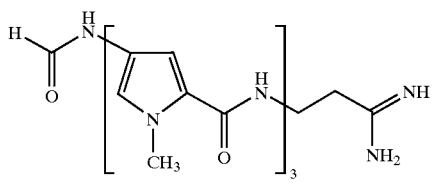

belongs to the family of the pyrroleamidine antibiotics and it is reported to interact reversibly and selectively with DNA-AT sequences, thus interfering with both replication and transcription. See, for a reference, Nature, 203, 1064 (1964); FEBS Letters, 7 (1970) 90; Prog. Nucleic Acids Res. Mol. Biol., 15, 285 (1975).

Several analogues to distamycin are known in the art as antitumor agents.

As an example, the international patent application WO 98/04524 in the name of the Applicant itself, discloses distamycin derivatives, having valuable biological properties as antitumor agents, wherein the distamycin formyl group is replaced by an acryloyl moiety and the amidino group is replaced by several nitrogen-containing ending groups, among which is guanidino.

Specific examples of this class of acryloyl-distamycin-guanidino derivatives, optionally in the form of pharmaceutically acceptable salts, for instance as hydrochloride salts, are:

N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide (internal code PNU 166196); and N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide.

These derivatives are prepared according to a chemical process comprising, essentially, the condensation reaction between a properly activated carboxylic acid derivative with a poly-pyrroleamido framework bearing the desired nitrogen-containing ending group, for instance the guanidino group.

This latter guanidino intermediate, in its turn, is prepared according to a rather troublesome step-by-step procedure which implies, substantially, several acylation reactions of 2-carboxy-4-amino-pyrroles which are obtained through reductions of the corresponding nitro derivatives, in a serial manner.

For a general reference to the above process for preparing acryloyl-distamycin derivatives, also including acryloyl-distamycin-guanidino derivatives see, for instance, the aforementioned WO 98/04524.

BRIEF SUMMARY OF THE INVENTION

In this respect, we have surprisingly found that the said acryloyl-distamycin-guanidines can be advantageously prepared through a chemical process which allows to obtain the desired products in high yields and purity and in a limited number of steps.

Therefore, it is a first object of the present invention a process for preparing a distamycin derivative of formula

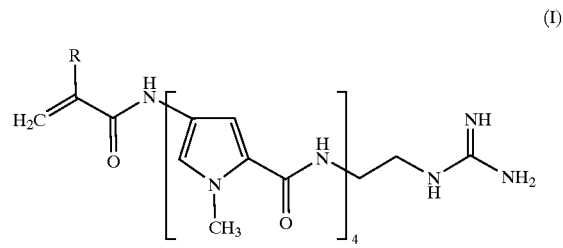

wherein R is a bromine or chlorine atom; or a pharmaceutically acceptable salt thereof; which process comprises:

a) reacting, under basic conditions, 2-amino-ethylguanidine with a compound of formula

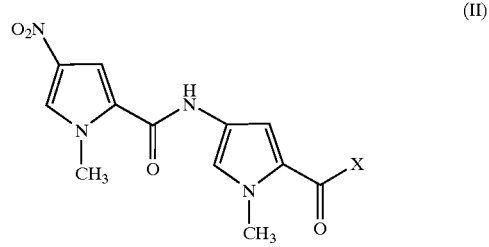

wherein X is hydroxy or a suitable leaving group, so as to obtain a compound of formula

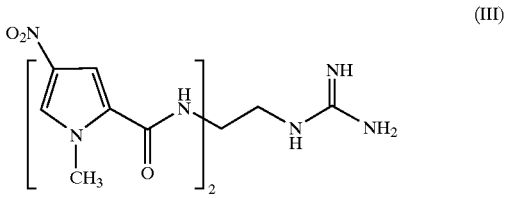

b) reducing the nitro-derivative of formula (III) to the corresponding amino-derivative and, subsequently, reacting the resultant amino-derivative with the above compound of formula (II), under basic conditions, so as to obtain a compound of formula (IV)

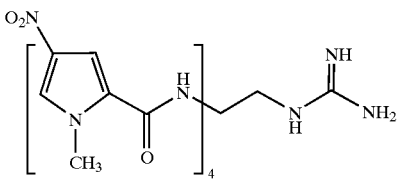

c) reducing the nitro-derivative of formula (IV) to the corresponding amino-derivative and, subsequently, reacting in the presence of a suitable condensing agent and under basic conditions the resultant amino-derivative with a compound of formula (V)

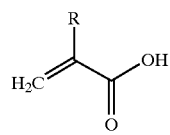

wherein R is a bromine or chlorine atom; so as to obtain the compound of formula (I) and, optionally, converting it into a pharmaceutically acceptable salt thereof.

The process object of the present invention allows to obtain the compounds of formula (I) under mild operative conditions, in high yields and purity.

In addition, it enables the preparation of the aforementioned compounds without the need of carrying out several steps and/or isolating many intermediates which could lead to undesired by-products.

DETAILED DESCRIPTION OF THE INVENTION

Preferably, the process of the invention is directed to the preparation of the compound of formula (I) wherein R is a bromine atom, that is the compound formerly indicated as PNU 166196. In this respect, it is clear to the man skilled in the art that within the general formula (I) compounds thus prepared, the possibility for the R group of being bromine or chlorine will depend upon the compound of formula (V) being used in step c).

According to the process object of the invention, the reaction of step a) is carried out between 2-amino-ethylguanidine, optionally in the form of a pharmaceutically acceptable salt, preferably as 2-amino-ethylguanidine dihydrochloride, and a slight excess, for instance from 1 to 2 equivalents, of the compound of formula (II).

Within the compounds of formula (II) the X group represents hydroxy or a suitable leaving group such as, for instance, bromine, chlorine, 2,4,5-trichlorophenoxy, 2,4-dinitrophenoxy, succinimido-N-oxy or imidazolyl.

Preferably, the X group is a bromine or chlorine atom.

The reaction is performed under basic conditions with from 1 to 4 equivalents of an organic or inorganic base such as, for instance, sodium or potassium hydroxide, carbonate or bicarbonate, or with an organic amine such as triethylamine, ethyldiisopropylamine, piperidine and the like.

Sodium carbonate or bicarbonate are preferably used. The reaction occurs in the presence of a suitable solvent such as, for instance, dioxane, tetrahydrofuran, dimethylsulfoxide, dimethylformamide, water and admixtures thereof.

According to a preferred embodiment of the process, step a) is preferably carried out in the presence of dioxane, tetrahydrofuran, water or admixtures thereof.

The reaction temperature may vary from about 0° C. to about 50° C. and for a time varying from about 1 to about 24 hours. The intermediate nitro-compound of formula (III) may be isolated, either as such or in the form of a pharmaceutically acceptable salt, for instance as hydrochloride salt, or may be further processed, without being isolated, under reductive conditions as per step b) of the process.

The reduction of the compound of formula (III), as per step b) of the process, is carried out according to well-known methods for reducing nitro-derivatives to amino-derivatives.

Typical reductive conditions include the use of conventional reducing agents such as, for instance, sodium hypophosphite, hydrazine, sulfides, polysulfides and the like, or catalytic hydrogenation.

According to a preferred embodiment of the invention, the compound of formula (III) is hydrogenated under heterogeneous catalytic conditions in the presence of platinum or palladium catalysts, for instance palladium on charcoal (Pd/C).

The hydrogenation reaction is preferably carried out in the presence of a suitable solvent, for instance dioxane, tetrahydrofuran, dimethylsulfoxide, dimethylformamide, water and admixtures thereof, at temperatures varying from about 0° C. to about 50° C., for a time of about 1 to about 24 hours and by employing from about 1 to about 10 bar (1 bar=$10^5$ Pa) of hydrogen pressure.

The amino-derivative thus obtained is further reacted, without being isolated, with the compound of formula (II). The reaction occurs under the above reported conditions as per step a). of the process, that is to say in the presence of a base and of a suitable solvent.

As formerly indicated, the intermediate nitro-compound of formula (IV) may be isolated, either as such or in the form of a pharmaceutically acceptable salt, for instance as hydrochloride salt, or may be further processed, without being isolated, in step c) of the process.

In step c), the reduction of the compound of formula (IV) is carried out according to well-known methods for reducing nitro-derivatives to amino-derivatives, as above reported. Preferably, the reaction is carried out under catalytic hydrogenation conditions in the presence of palladium or platinum catalysts, as set forth above.

The resultant amino-derivative is then reacted, without being isolated, with a compound of formula (V) according to conventional methods for the acylation of amino derivatives.

In particular, the reaction is performed in the presence of a solvent such as, for instance, dioxane, tetrahydrofuran, water, dimethylsulfoxide, dimethylformamide or admixtures thereof, in the presence of a conventional condensing agent and of an inorganic or organic base such as, for instance, sodium or potassium hydroxide, carbonate or bicarbonate, or with an organic amine such as, for instance, triethylamine, ethyldiisopropylamine, piperidine and the like.

Preferred condensing agents are, for instance, N,N'-dicyclohexylcarbodiimide (DCC) or (N'-(3-dimethylaminopropyl)-N-ethylcarbodiimide) hydrochloride (EDC).

The reaction temperature may vary from about −10° C. to about 50° C. and for a time varying from about 1 to about 24 hours. As formerly indicated, the preparation of the compound of formula (I) wherein R is a bromine atom (PNU 166196), as per step c) is carried out with a compound of formula (V) wherein R is a bromine atom.

According to a preferred embodiment of the invention, the whole process can be carried out in the presence of a unique reaction solvent, for instance dioxane, tetrahydrofuran, water or admixtures thereof.

As such, it is clear that by carrying out the whole process in the same reaction solvent, volumes and, hence, large amounts of solvent to be recovered, are dramatically reduced.

According to a particularly preferred embodiment of the invention, all the reaction steps from a) to c) can be carried out in one pot without the need of isolating any intermediate.

In this respect, each of the reactions defined in steps from a) to c) are performed as follows, by first reacting a compound of formula (II) with 2-amino-ethylguanidine dihydrochloride so as to obtain a compound of formula (III), by reducing the compound of formula (III) to the corresponding amino-derivative and by subsequently reacting it with, again, the compound of formula (II) so as to obtain the compound of formula (IV) and, finally, by reducing it to the amino-derivative and by reacting this latter with the compound of formula (V).

Given the above, it is also clear to the man skilled in the art that, whenever desired, each, or at least some, of the aforementioned reactions can be alternatively accomplished by separating any intermediate compound.

So far, any of the aforementioned approaches of the process for preparing the compounds of formula (I) are within the scope of the present invention.

Finally, the conversion of the distamycin derivative of formula (I) into a pharmaceutically acceptable salt or, on the other side, the conversion of a salt thereof into the free compound, may be carried out according to well known techniques.

Examples of pharmaceutically acceptable salts of the compounds of formula (I) are the acid addition salts with pharmaceutically acceptable acids such as, for instance, hydrochloric, hydrobromic, sulfuric, nitric, acetic, trifluoroacetic, propionic, succinic, malonic, citric, tartaric, methanesulfonic, p-toluensulfonic acid and the like.

The compound 2-ethyl-aminoguanidine, for instance as dihydrochloride salt, is a known compound which can be prepared according to known methods; see, for instance, Syntethic Communications 20(16), 2559–2564 (1990).

The compound of formula (II) is known or can be easily prepared according to known methods; for a reference to the preparation of the compound of formula (II) wherein X is hydroxy see, as an example, U.S. Pat. No. 4,942,227.

The compound of formula (V), in its turn, is a commercially available compound.

From the above, it is worth noting that the process of the invention allows to perform a set of subsequent reactions by using a limited number of reactive derivatives.

The compound of formula (II), in fact, is very conveniently used in two different reactions of the process: first, as a starting material with 2-aminoethylguanidine dihydrochloride, in step a), and subsequently as a reactive intermediate in step b).

The intermediate compound of formula (IV) is novel and, hence, represents a further object of this invention. As formerly indicated, the compounds of formula (I) are useful in therapy as antitumor agents.

For a general reference to the antitumor activity of the compounds of formula (I) see the aforementioned WO 98/04524.

According to a practical embodiment of the process of the invention for preparing the compound of formula (I) wherein R is a bromine atom (PNU 166196), a proper amount of 2-amino-ethylguanidine dihydrochloride is reacted, in a solvent system preferably comprising dioxane, tetrahydrofuran, water or admixtures thereof and in the presence of a base, for instance an inorganic base such as sodium carbonate or bicarbonate, with a proper amount, preferably a slight excess, of the compound of formula (II).

The reaction is carried out under mild operative conditions and the resultant nitro-derivative of formula (III) is first hydrogenated under heterogeneous catalytic conditions, in the presence of palladium on charcoal, and subsequently reacted with a proper amount, preferably a slight excess, of the compound of formula (II), under basic conditions.

The resultant compound of formula (IV) is then hydrogenated as above described to the corresponding amino-derivative which is further reacted, in the presence of a base and of a condensing agent, for instance EDC, with α-bromoacrylic acid of formula (V).

The desired compound of formula (I) thus obtained is then isolated in high yields and purity, according to conventional methods.

With the aim of illustrating the present invention, without posing any limitation to it, the following examples are now given.

EXAMPLE 1

Preparation of Tert-butyl-N-(2-aminoethyl)carbamate

Ethylendiamine (7 moles) was loaded into a reaction flask containing dioxane (2.7 l). Di-tert-butyl-dicarbonate (1.0 mole) in dioxane (270 ml) was subsequently added.

The reaction mixture was stirred at room temperature for 1 day and the solvent was then removed under vacuum.

Water (1.8 l) was added to the crude and the mixture was extracted with dichloromethane. The organic solvent was distilled off from the organic phase thus yielding the title compound (145 g; 90% yield).

EXAMPLE 2

Preparation of 2-aminoethyl-guanidine dihydrochloride

Tert-butyl-N-(2-aminoethyl)carbamate (0.4 moles), O-methylisourea hydrogenosulphate (0.8 moles) and triethylamine (2.5 moles) were loaded into a reaction flask containing a methanol:water=1:1 mixture (3 l).

The reaction mixture was stirred at room temperature for one day and the solvent was then removed under vacuum.

The crude was treated with ethanol (2 l) and gaseous hydrochloric acid (3.5 M) at 20° C. for 4 hours and subsequently filtered and dried, thus yielding the title compound (55 g; 74% yields).

EXAMPLE 3

Preparation of N-methyl-4-aminopyrrole-2-carboxylic acid

N-methyl-4-nitropyrrole-2-carboxylic acid (0.58 moles), hydrochloric acid 2N (350 ml) and Pd/C (5 g) were added to a dioxane:water=2:1 mixture (1.2 l).

The mixture was hydrogenated into a 2 l hydrogenation reactor at room temperature for 4 hours. The catalyst was filtered off, the solvent concentrated under vacuum and the resultant suspension was filtered.

The crude was dried yielding the title compound (94 g; 92% yield) as a white powder.

EXAMPLE 4
Preparation of N-methyl-4-nitropyrrole-2-carboxyxlic acid chloride

Thionyl chloride (3.16 moles) was loaded into a reaction flask containing N-methyl-4-nitropyrrole-2-carboxylic acid (1.17 moles) in toluene (1.5 l).

The reaction mixture was stirred for 3 hours at 100° C., cooled and subsequently concentrated under vacuum.

The resulting suspension was treated with cyclohexane for 2 hours at room temperature, then filtered and dried yielding the title compound (200 g; 96% yield).

EXAMPLE 5
Preparation of N-methyl-4-[(N'-methyl-4-nitro-pyrrolyl-2yl) carbonylamino]pyrrole-2-carboxylic acid N-methyl-4-aminopyrrole-2-carboxylic acid (0.56 mole), prepared as described in example 3, and sodium bicarbonate (2 moles) were loaded into a reaction flask containing a dioxane:water=1:1 admixture (300 ml).

A solution of N-methyl-4-nitropyrrole-2-carboxylic acid chloride (0.62 moles), prepared as described in example 4, in dioxane (350 ml) was then added therein.

The reaction mixture was stirred for 1 hour at room temperature, then water (100 ml) was added.

A solution 2N of hydrochloric acid was then added up to pH 3 and the organic solution was concentrated under vacuum until dioxane was completed removed The suspension was filtered yielding the title compound (147 g; 90% yield).

EXAMPLE 6
Preparation of N-methyl-4-[(N'-methyl-4-nitro-pyrrolyl-2-yl)carbonylamino]pyrrole-2-carboxylic acid chloride N-methyl-4-[(N'-methyl-4-nitro-pyrrolyl-2-yl) carbonylamino]pyrrole-2-carboxylic acid (0.45 moles), prepared as described in example 5, dimethylformamide (3 ml) and thionyl chloride (2.3 moles) were loaded into a reaction flask containing dichloromethane (2.5 l).

The resultant suspension was stirred for 6 hours at refluxing temperature, then cooled at room temperature and filtered.

The crude was treated with hexane (1 l), then filtered and dried yielding the title compound (163 g; 90% yield).

EXAMPLE 7
Preparation of N-methyl-4-[(N'-methyl-4-nitro-pyrrolyl-2-yl)carbonylamino]pyrrole-2-carboxylic acid chloride ethylguanidine hydrochloride.

N-methyl-4-[(N'-methyl-4-nitro-pyrrolyl-2-yl) carbonylamino]pyrrole-2-carboxylic acid chloride (0.057 moles), prepared as described in example 6, was loaded into a reaction flask containing dioxane (300 ml).

Then, a solution of 2-aminoethyl-guanidine dihydrochloride (0.057 moles), prepared as described in example 2, and sodium bicarbonate (0.17 moles) in water (100 ml) were added therein.

The suspension was stirred for 2 hours at room temperature. A solution 2N of hydrochloric acid (60 ml) and Pd/C (3 g) were subsequently added.

The mixture was then hydrogenated into a 2 l hydrogenation reactor at room temperature for 3 hours and then filtered.

The resultant solution was then added to a suspension of N-methyl-4-[(N'-methyl-4-nitro-pyrrolyl-2-yl) carbonylamino]pyrrole-2-carboxylic acid chloride (0.057 moles) in dioxane (120 ml). Sodium bicarbonate (0.17 moles) was then added and the suspension was stirred at room temperature for 4 hours.

The mixture was then concentrated under vacuum until a suspension was obtained and the resulting suspension was cooled at room temperature and filtered.

The wet crude was treated with acetone, filtered and dried thus yielding the title compound (30 g; 85% yield).

EXAMPLE 8

Preparation of 2-[1-methyl-4-[1-methyl-4-[1-methyl-4-(1-methyl-aminopyrrole-2-carboxamido)pyrrole-2-carboxamido]pyrrole-2-carboxamido]pyrrole-2-carboxamido]ethylguanidine hydrochloride The compound of example 7 (0.067 moles), dioxane (550 ml), water (450 ml), a solution 2N of hydrochloric acid (120 ml) and Pd/C (13 g) were loaded into a hydrogenation reactor.

The suspension was hydrogenated at room temperature for 3 hours, then the mixture was filtered.

The resultant solution was treated with acetone (1300 ml), cooled overnight at 4° C. and filtered.

The crude was dried thus yielding the title compound (40 g; 90% yield.

EXAMPLE 9

Preparation of N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]carbonyl-1-methyl-1H-pyrrole-2-carboxamide hydrochloride (internal code PNU 166196A).

Bromoacrylic acid (7.56 mmoles), EDC (7.56 mmoles), sodium bicarbonate (14.3 mmoles) and dioxane (60 ml) were loaded into a reaction flask.

The compound of example 8 (2 mmoles) and a mixture of dioxane:water 2:1 (30 ml) were then added. The mixture was stirred for 1 hour at room temperature and a solution 2 N of hydrochloric acid was then added up to pH 4.5.

The solvent was then concentrated under vacuum, the suspension was filtered and the resultant crude was dried yielding the title compound (1.3 g; 85% yield; HPLC Area>98%).

What is claimed is:

1. A process for preparing a distamycin derivative of formula (I)

wherein R is a bromine or chlorine atom; or a pharmaceutically acceptable salt thereof; which process comprises:

a) reacting, under basic conditions, 2-amino-ethylguanidine with a compound of formula

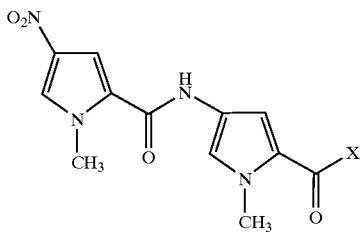

(II)

wherein X is hydroxy or a suitable leaving group, so as to obtain a compound of formula

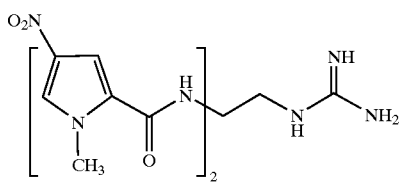

(III)

b) reducing the nitro-derivative of formula (III) to the corresponding amino-derivative and, subsequently, reacting the resultant amino-derivative with the above compound of formula (II), under basic conditions, so as to obtain a compound of formula

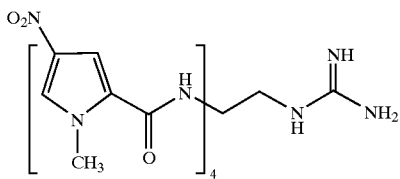

(IV)

c) reducing the nitro-derivative of formula (IV) to the corresponding amino-derivative and, subsequently, reacting in the presence of a suitable condensing agent and under basic conditions the resultant amino-derivative with a compound of formula

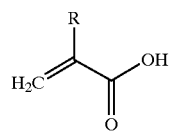

(V)

wherein R is a bromine or chlorine atom; so as to obtain the compound of formula (I) and, optionally, converting it into a pharmaceutically acceptable salt thereof.

2. A process according to claim 1 for the preparation of the compound of formula (I), or a pharmaceutically acceptable salt thereof, wherein R is a bromine atom.

3. A process according to claim 1 wherein steps a) to c) are carried out in one pot without isolating any reaction intermediate.

4. A process according to claim 1 wherein, in step a), 2-amino-ethylguanidine is in the form of its dihydrochloride salt.

5. A process according to claim 1 wherein, within the compound of formula (II) of step a), X is hydroxy or a group selected from bromine, chlorine, 2,4,5-trichlorophenoxy, 2,4-dinitrophenoxy, succinimido-N-oxy or imidazolyl.

6. A process according to claim 5 wherein X is a bromine or chlorine atom.

7. A process according to claim 1 wherein the reductive steps under b) or c) are carried out in the presence of a reducing agent selected from the group consisting of sodium hypophosphite, hydrazine, sulfides, and polysulfides or as catalytic hydrogenation reactions.

8. A process according to claim 7 wherein the reductive steps b) or c) are carried out as catalytic hydrogenation reactions in the presence of palladium or platinum hydrogenation catalysts.

9. A process according to claim 1 wherein, in step c), the reaction between the resultant amino derivative and the compound of formula (V) is carried out in the presence of a suitable condensing agent selected from the group consisting of N,N'-dicyclohexylcarbodiimide (DCC) or (N'-(3-dimethylaminopropyl)-N-ethylcarbodiimide) hydrochloride (EDC).

10. A process according to claim 1 wherein any reaction performed under basic conditions is carried out in the presence of an inorganic or organic base.

11. A process according to claim 10 wherein the base is sodium or potassium hydroxide, carbonate or bicarbonate, triethylamine, ethyldiisopropylamine or piperidine.

12. A process according to claim 1 wherein the reactions of steps a) to c) are, each independently, carried out in the presence of a suitable reaction solvent selected from the group consisting of dioxane, tetrahydrofuran, dimethylsulfoxide, dimethylformamide, water or admixtures thereof.

13. A process according to claim 12 wherein the reaction solvent is selected from the group consisting of dioxane, tetrahydrofuran, water and admixtures thereof.

14. A process according to claim 1 wherein said pharmaceutically acceptable salts of the compounds of formula (I) are the acid addition salts of pharmaceutically acceptable acids selected from the group consisting of hydrochloric, hydrobromic, sulfuric, nitric, acetic, trifluoroacetic, propionic, succinic, malonic, citric, tartaric, methanesulfonic and p-toluensulfonic acid.

15.

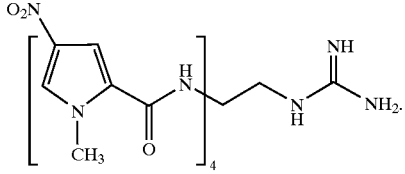

* * * * *